United States Patent [19]
Cawood

[11] Patent Number: 5,766,136
[45] Date of Patent: Jun. 16, 1998

[54] MIDSTREAM URINE COLLECTOR WITH DEFLECTION SHIELD

[76] Inventor: Charles David Cawood, 11527 N. Lou A1 Ct., Houston, Tex. 77024

[21] Appl. No.: 766,754

[22] Filed: Dec. 13, 1996

Related U.S. Application Data

[63] Continuation-in-part of Ser. No. 399,071, Mar. 8, 1995.
[51] Int. Cl.$^6$ .................................................. A61B 5/00
[52] U.S. Cl. ............................................................ 600/573
[58] Field of Search ................................. 600/573, 574, 600/580; 604/349

[56] References Cited

U.S. PATENT DOCUMENTS

| | | | |
|---|---|---|---|
| 3,886,112 | 5/1975 | Watson et al. | 260/33.4 R |
| 3,934,578 | 1/1976 | Godron | 128/284 |
| 4,136,798 | 1/1979 | Oberstein | 220/408 |
| 4,372,311 | 2/1983 | Potts | 128/287 |
| 4,557,274 | 12/1985 | Cawood | 128/760 |
| 5,178,469 | 1/1993 | Collinson | 383/1 |
| 5,205,473 | 4/1993 | Coffin, Sr. | 229/1.5 B |
| 5,318,549 | 6/1994 | Yang | 604/349 |

*Primary Examiner*—Max Hindenburg
*Attorney, Agent, or Firm*—Tilton Fallon Lungmus

[57] ABSTRACT

A midstream urine collector is disclosed having an open-ended funnel-shaped body with a cup mounted therein, the cup having an upwardly-directed mouth over which a cover of water-soluble material extends. The cup is substantially smaller than the flow passage through the body so as to permit the downward flow of urine through the passage past the cup. A deflector in the form of a disc-shaped shield is mounted within the funnel-shaped body above the water-soluble cover to protect the cover against rupture that might otherwise occur if the cover were impacted squarely by a forceful stream of urine as a patient commences voiding into the collector.

11 Claims, 1 Drawing Sheet

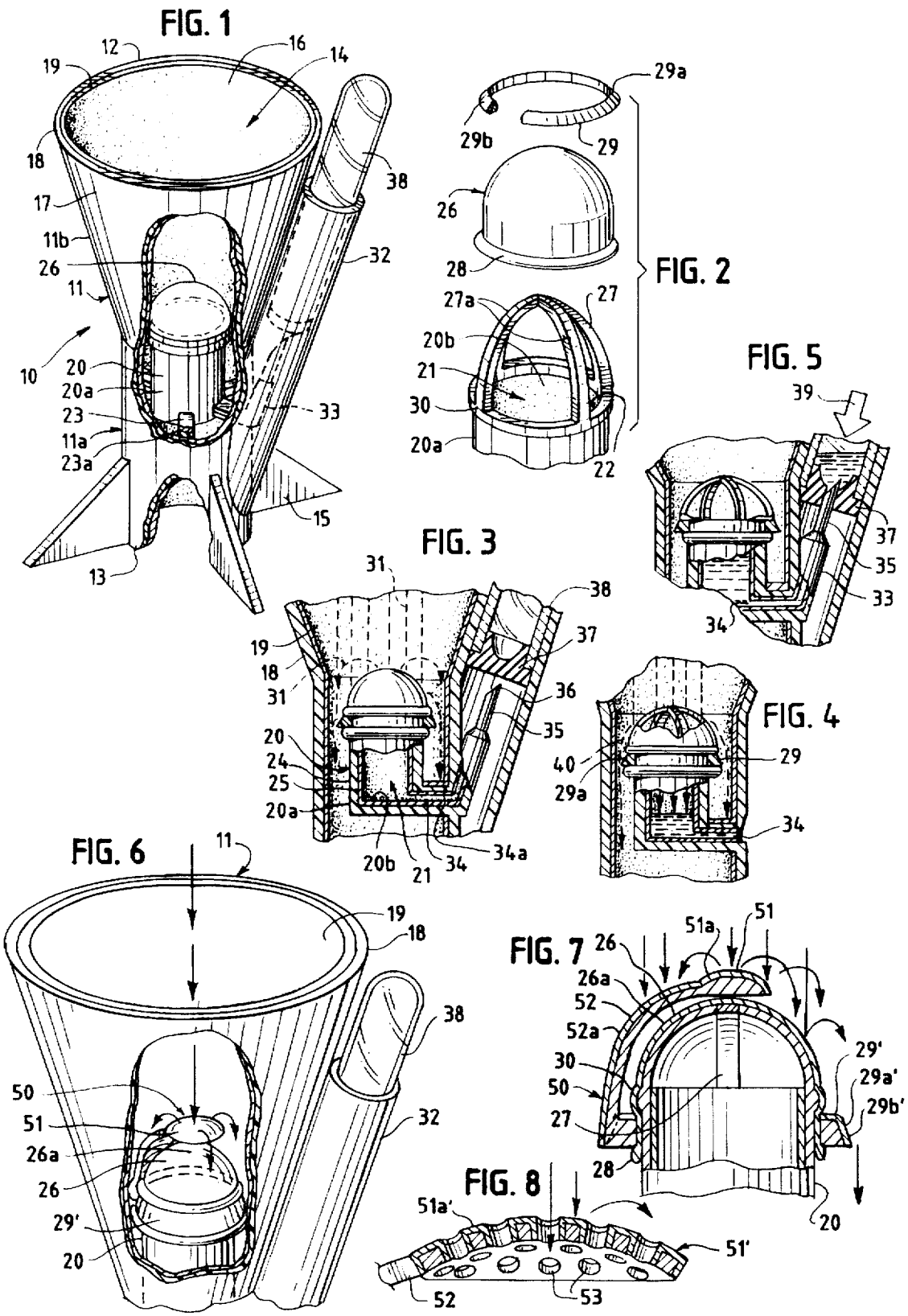

MIDSTREAM URINE COLLECTOR WITH DEFLECTION SHIELD

RELATED APPLICATION

This application is a continuation-in-part of copending application Ser. No. 08/399,071, filed Mar. 8, 1995.

BACKGROUND AND SUMMARY

Conventional urine sample collectors generally take the form of a simple cup which includes a closable lid. Typically, the patient voids into the cup, closes the lid, and then returns it to a nurse who must wear gloves to pick up, label, and place the cup in a plastic zip-lock bag for transport to a laboratory for analysis. The sample container must then be disposed of through a certified medical waste disposal company which follows stringent and expensive disposal standards. Handling of the sample container must be carefully conducted throughout the entire process since diseases such as aids or hepatitis can be transmitted by improper handling of urine specimens.

Conventional sample cups also present problems with respect to the sample being contaminated by the initial portion of the urine stream. The importance of collecting a "midstream" sample for urine analysis is well known. A particularly advantageous device for collecting a midstream sample is disclosed in my U.S. Pat. No. 4,557,274. Briefly, the device includes a tubular body through which a patient voids and a cup member is positioned in the flow passage of the tubular body which bypasses the initial and terminal portions of the urine stream but collects a midstream sample. The sample can then be simply transferred from the cup member to a conventional air-evacuated collection tube or conventional syringe. While this device presents an effective way of collecting a midstream urine sample, there still exists a need in the industry for a device which overcomes the complexity and cost of handling and disposal of urine sample collection devices.

Copending application Ser. No. 08/399,071 discloses an uncomplicated low-cost midstream urine collector which is adapted for one time use and which is discardable in a common toilet bowl and waste water system without obstructing or damaging the water discharge lines. More specifically, the collector automatically bypasses the contaminated initial portion of the stream and then collects a sterile or at least relatively uncontaminated midstream sample which is quickly and easily transferred to a sterile collection tube. The collector is primarily composed of a water-soluble material which gives the device its structural integrity and, when the device is discarded in the water of a toilet bowl, it readily dissolves or disperses so that it may be flushed through the water discharge lines of a waste water system without obstructing or damaging the system. Protective layers of water-insoluble material line or coat the majority of the surfaces of the device which are exposed to urine when a patient voids into the device. However, the protective layers are thin and relatively weak so that they will breakup or disperse once the primary water-soluble components of the collector dissolve. Such a construction is low-cost in design and is suitable for manufacturing and marketing as a disposable item for one-time use and subsequent disposal in a flush toilet.

In brief, the flushable midstream urine collector includes a funnel-shaped tubular body which defines a flow passage and a cup member which is disposed in the flow pasage. Cover means are provided for effectively sealing the mouth of the cup member in a first operative state so that the initial portion of the urine stream is deflected and for exposing the mouth of the cup member in a second operative state so that the mouth of the cup member is exposed to receive an uncontaminated subsequent midstream portion. The tubular body and cup member are composed of primary layers of water-soluble material which provide the structural components of the device and which will dissolve or disperse when disposed in the water of a toilet bowl. Thin protective, but relatively weak, layers of water-insoluble material line the inner surfaces of the tubular body and cup member to prevent premature dissolution of the primary layers when a patient voids into the collector. When the device is disposed in the water of a toilet bowl, the primary layers of the tubular body and cup member dissolve or disperse so that the device loses its structural integrity and the relatively weak protective layers collapse and disperse so that the entire collector is readily flushable. The primary layers of the tubular body and the cup member may be composed of a relatively rigid water-soluble polymer such as polyvinyl alcohol. The protective layers of water-soluble material may be composed of wax, polyvinyliodine, or other thin water-insoluble materials which are relatively weak and which will break-up or disperse upon dissolution of the primary layers.

The inner surface of the cup member is provided with a protective layer of water-insoluble material to contain the midstream sample. However, the outer water-soluble surface of the cup member must be left exposed to the flow passage; otherwise, if both the inner and outer surfaces of the cup member were protected by water-insoluble material, the cup member would not dissolve or disperse when disposed in the water of a toilet bowl. Accordingly, urine passing through the passage will contact the water-soluble outer surface of the cup member. However, it is believed that the contact between the urine and primary layer occurs only randomly and that the fluid does not directly contact the primary layer for a sufficient amount of time to compromise the structural integrity of the cup member. For example, a patient will typically void into the collector for a period of approximately 30–60 seconds whereas the primary layer requires generally at least 2 minutes of direct and constant exposure to fluid, preferably 2–5 minutes, in order to completely dissolve or disperse.

While the collectors of the aforementioned patent and application are generally effective in collecting midstream samples, after allowing the contaminated initial portions of the streams to bypass the collection cups, it has been found that the process of collecting an uncontaminated midstream sample may be defeated if the water-soluble membrane or cover extending over the mouth of the cup tears or ruptures because of the forceful and direct impact from urine early in the voiding process. A main aspect of this invention therefore lies in providing urine deflecting means mounted within the funnel-shaped body above the relatively fragile membrane or cover for shielding at least an upper portion of the dome-shaped cover against direct or frontal impact from a stream of urine discharged into the collector.

In one embodiment, the deflecting means takes the form of a disc-shaped shield that is generally imperforate and is centered directly over the dome-shaped cover. Another embodiment is similar but has openings or perforations extending therethrough. The effect in either case is to shield the covering membrane from direct impact by an initial urine stream that might otherwise tear or rupture the membrane. The deflected urine may impinge on the inside surfaces of the funnel-shaped body and, after being so deflected, may contact the covering membrane to commence the dissolution action. By the time the membrane is dissolved, or partially dissolved, in about 2 to 15 seconds, initial flow has bypassed the cup and an essentially uncontaminated midstream sample may be collected by the cup and transferred to an air-evacuated collection tube. The collector includes support means for supporting a collection tube and evacuation passage means extends between the cup member and the support means. The collection tube may take the form of an air-evacuated collection tube having a piercable stopper that is slidably supported by the support means adjacent to a hollow spike communicating with the evacuation passage means. After a patient has finished voiding, the collector is simply placed upon an unyielding support surface and the evacuator tube is urged axially to cause piercing of the stopper and the flow of at least a portion of the midstream sample into the sterile tube.

The urine deflection shield is operative to protect the frangible membrane covering the mouth of the cup whether the collector is a flushable one, constructed to dissolve in the water of a toilet bowl into which it has been discarded, or is instead of non-flushable construction, being formed of materials that will not dissolve or disintegrate when exposed to water. If the collector is designed to be flushable, then the support means for the collection tube may be composed entirely of a water-soluble material so that it will dissolve or disperse when disposed in the water of a toilet bowl. Likewise, the evacuation passage means may be primarily composed of a water-soluble material except for a thin protective layer of water-insoluble material which lines the interior passage that extends in communication between the cup member and support means. The hollow spike may be composed of a water-insoluble material such as a rigid plastic or metal. However, the spike is would be preferably constructed to have a relatively short length of approximately 0.5 to 1.5 inches, preferably about one inch, so that it may be flushed into a common flush toilet without obstructing the water discharge lines. Once a nurse has extracted a urine sample from the collector with a collection tube, the collector is discarded into the water of a toilet bowl. After a sufficient interval has elapsed so that the primary layers of the tubular body and cup member, as well as the support means and evacuation passage means, dissolve and disperse, the toilet can then be flushed for permanent disposal of the collector.

Other features, objects, and advantages of the invention will become apparent from the specification and drawings.

DRAWINGS

FIG. 1 is a perspective view of a flushable midstream urine collector.

FIG. 2 is an exploded fragmentary perspective view illustrating a portion of the cup member and one embodiment of the cover means.

FIG. 3 is a fragmentary vertical sectional view illustrating the construction of the water-soluble and water-insoluble layers of the device and depicting operation of the device at the beginning of a sample-collecting procedure.

FIG. 4 is a sectional view similar to FIG. 3 but illustrating the device after the cover member has started to disintegrate and a midstream samplehas begun to enter the cup member.

FIG. 5 is a sectional view similar to FIGS. 3 and 4 but illustrating the further step of transferring the midstream sample from the cup member to an evacuated collection tube.

FIG. 6 is a fragmentary perspective view of a midstream urine collector embodying the present invention, such collector being equipped with a protective deflection shield.

FIG. 7 is a fragmentary vertical sectional view of the cup member of FIG. 6 equipped with the deflection shield.

FIG. 8 is an enlarged vertical sectional view of a modified shield having openings or perforations therethrough.

DETAILED DESCRIPTION OF PREFERRED EMBODIMENTS

Referring to FIGS. 1–5 of the drawings, the numeral 10 generally designates a flushable midstream urine collector which includes a tubular body 11 having an upper inlet 12, a lower outlet 13, and a flow passage 14 extending therebetween. The body is funnel-shaped, the lower section 11a of the body being generally cylindrical and the upper section 11b being frusto-conical in configuration. The lower section 11a is provided with a plurality of outwardly projecting legs 15 so that the collector may be placed in an upstanding position upon a tabletop or other support surface. A particularly advantageous construction of a midstream urine collector, although non-flushable, is disclosed in my U.S. Pat. No. 4,557,274, which is hereby incorporated by reference.

The tubular body 11 includes inner and outer surfaces 16 and 17 and inner surface 16 defines flow passage 14. The tubular body is composed of a primary outer layer 18 of a water-soluble polymeric material which will dissolve or disperse when disposed in the water of a toilet bowl and a thin inner protective layer 19 of a water-insoluble material which lines inner surface 16 of the body and prevents urine flowing through the passage from contacting the water-soluble primary layer of the body. Outer layer 18 forms the structural components of the tubular body and may be formed from water-soluble polymers which are capable of being formed into rigid or semi-rigid articles. One particularly suitable water-soluble material is polyvinyl alcohol which is commercially available in pelletized form and which may be injection molded at low temperatures to form the tubular body. However, it will be understood that other water-soluble polymeric materials may be effective, such as polyethylene oxide or carboxymethyl cellulose. In any event, it is believed preferable if the water-soluble material requires at least about 2 minutes of direct exposure to a fluid in order to significantly dissolve or disperse. Preferably, the water-soluble material is constructed so that it will dissolve or disperse in a period of about 2–5 minutes after it is discarded in the water of a toilet bowl. However, water-soluble materials which may require up to a period of about 10 minutes to dissolve are still believed to be suitable as leaving the collector in the toilet bowl for such a time period is usually not inconvenient in a typical situation in which a patient is providing a urine sample.

Unlike the primary layer of the tubular body, the inner protective layer 19 is relatively thin and weak and serves primarily as a protective coating to prevent direct exposure of the primary layer to fluids flowing through the passage of the tubular body. The inner protective layer lacks sufficient strength to maintain its structural integrity when the primary layer of the tubular body dissolves or disperses and will readily collapse and disperse upon dissolution of the primary layer. The protective layer may be formed from water-insoluble polymeric materials such as polyvinyl chloride or polyvinyliodine, or other suitable water-insoluble materials known in the art. One particularly suitable water-insoluble material is wax which may be easily applied by spray coating a thin layer of wax onto the inner surface of the tubular body.

Within the flow passage 14 of body 11 is a cup member 20. The cup member includes an outer surface 20a which is exposed to the flow passage and an inner surface 20b which defines an interior chamber 21 positioned below an upwardly-directed mouth 22. The cup member is preferably mounted within the upper portion of the body's lower section 11a, and bridging means in the form of struts 23 support the cup member within the flow passage. The cup member is substantially smaller than the body and, in particular, has an outer diameter smaller than the inside diameter of body 11. Consequently, fluid entering the inlet of the funnel-shaped body may flow downwardly through passage 14 past cup member 20 and may be discharged through outlet 13.

The cup member is composed of a primary layer 24 of water-soluble material which will dissolve or disperse when disposed in the water of a toilet bowl and the primary layer of the cup member may have the same, or a similar, construction as the primary layer of the tubular body. The cup member also includes a thin protective, but relatively weak, layer 25 of water-insoluble material which lines the inner surface 20b of the cup member and prevents fluid collected in chamber 21 from contacting the primary layer 24 of the cup member. Protective layer 25 may have the same, or a similar, construction as the protective layer which lines the inner surface of the tubular body.

The struts 23 which support cup member 20 in the flow passage are primarily composed of a water-soluble material except for a thin layer 23a of water-insoluble material which faces inlet 12 and deflects fluid entering and flowing through the passage away from the primary water-soluble component of the struts. It will be understood that at least a portion of the water-soluble component of the struts should remain exposed to the passage so that, when the collector is discarded in the water of a toilet bowl, the water will contact and initiate dissolution of the primary component of the struts.

It will also be noted that outer surface 20a of cup member 20 is formed from water-soluble primary layer 24 which is exposed to fluids flowing through the passage; otherwise, if the outer and inner surfaces of the cup member were coated with a water-insoluble material, the cup member would be completely insulated and would not dissolve or disperse in the water of a toilet bowl. Although the water-soluble outer surface of the cup member is exposed to the fluid passage, it is believed that fluids passing through the passage will not cause significant disintegration or dissolution of the cup member. This is because fluids passing through the passage only randomly contact the outer surface of the cup member, and such contact only occurs during the limited period of time that the patient voids into the collector, which is typically a period of about 30 to 60 seconds. In contrast, the primary layer of the cup member, as well as the primary layer of the tubular body, are preferably constructed of a water-soluble material which requires at least about 2 minutes of direct exposure to a fluid in order to significantly dissolve or disperse. When the collector is discarded in the water of a toilet bowl, the water in the bowl envelopes the collector and initiates dissolution of the exposed primary layer 18 of the tubular body and the exposed primary layer 20a of the cup member so that within approximately 2–10 minutes, preferably 2–5 minutes, the primary layers of the collector lose their structural integrity. The relatively weak protective layers then collapse or disintegrate so that the entire collector is readily flushable through a common flush toilet without obstructing or otherwise damaging the discharge lines of the water disposal system.

Cover means 26 extend over the mouth 22 of cup member 20. In the construction shown in FIGS. 1–5, the cover is formed entirely, or substantially so, of a non-contaminating water-soluble material capable of rapidly disintegrating upon direct exposure to an aqueous fluid (urine). The cover is shown to be generally dome-shaped, presenting a convexly curved or sloping upper surface capable of deflecting fluid entering the flow passage of the body and preventing the fluid from initially entering cup member 20. To maintain the cover in its dome configuration, cup member 20 may be provided with a framework of arched supporting struts 27. The struts are primarily formed from a non-contaminating water-soluble polymeric material which may be the same, or similar to, the primary layers of the tubular body and cup member. However, the uppermost portion or upwardly-directed surfaces 27a of the struts which support the cover are provided with a thin protective layer of water-insoluble material to prevent the struts from significantly disintegrating when a patient voids into the collector. While the unprotected surfaces of the struts will come into random contact with the urine stream, it is believed that the thin protective layer 27a of water-insoluble material is sufficient to deflect the stream and prevent prolonged direct contact between the stream and the structural components of the struts so that only a minimal portion of the struts may dissolve during use and flow into the cup member. However, like the cover itself, the struts are formed of a non-contaminating water-soluble polymeric material which will not effect the sample that is collected.

Attaching means are provided for securing the cover over the mouth of the cup member. The attachment means may take the form of a circumferential beaded portion 28 provided on the cover so that the cover may be locked into place upon the cup member by a resilient collar 29 disposed about the cover, between the bead 28 and the annular flange or rim 30 about the mouth of the cup member, in the manner depicted most clearly in FIG. 3. Collar 29 is preferably composed primarily of a water-soluble material which may be the same as or similar to the primary layers of the tubular body and cup member. However, collar 29 includes a thin protective layer 29a of water-insoluble material on its uppermost surfaces which face inlet 12 of the tubular body for preventing the primary water-soluble component of collar 29 from prematurely dissolving when a patient voids into the device.

Operation of the cover means between a first operable state in which it seals the mouth of the cup member and deflects the initial portion of urine stream and a second operative state in which it exposes the mouth of the cup member for collection of a subsequent midstream sample will now be described. As stated, cover 26 consists essentially of a thin membrane formed of water-soluble polymeric material, and such material should not contaminate the fluid that contacts and dissolves it. The term "non-contaminating" is used here to mean any material that when dissolved in a fluid sample will not have any significant effect on the results of tests that may subsequently be performed on that sample. A particularly effective material for such purposes has been found to be a polyvinyl alcohol film of the type marketed by Polymer Films, Inc., Rockville, Conn., under the designation PVOH 17-35-1; however, other water-soluble non-contaminating polymeric materials might be used such as, for example, methyl cellulose and derivatives thereof. The thickness of the film or membrane may be varied depending on the material used but, in any event, the composition and thickness of the membrane should be such that disintegration of the cover commences within a period of about 2 to 15 seconds when the cover is directly exposed to a stream of urine. Preferably, such disintegration should commence within about 3 to 8 seconds. Consequently, when a patient voids into the sterile tubular collector, the initial contaminated portion of the stream (contaminated by the labia in the female and the foreskin and distal urethra in the male) is deflected by the cover and bypasses cup member 20. Such deflected bypassing flow is represented by arrows 31 in FIG. 3. After a few seconds, the membrane cover 26 begins to disintegrate, allowing a midstream portion of the flow to enter the cup member (FIG. 4). Complete bypassing of the cup member again occurs after that member has become completely filled with the relatively uncontaminated midstream portion of the flow of urine. Once urination is completed, the midstream portion remains collected in the cup member, with the beginning and terminal portions of the stream having been passed through the funnel-shaped body and into the toilet bowl.

Means are provided for extracting a sample from the cup member and transferring such sample to a sterile collection tube. More specifically, support means 32 are provided as part of the tubular body 11 and an evacuation passage means 33 defines an interior passage 34 which extends in communication between the support means and the cup member. The support means and evacuation passage means are formed almost entirely, or substantially so, of a water-soluble material which will dissolve or disperse when disposed in the water of a toilet bowl. Preferably, the support means and evacuation passage means are formed from the same material as the primary layers of the tubular body and cup member. As mentioned, pelletized water-soluble polymers such as polyvinyl alcohol may be injection molded at low temperatures to form the unitary device. Consequently, all of the substantial components of the collector are formed from a water-soluble polymer which will dissolve or disperse in the water of a toilet bowl and the remainder of the device is formed from thin protective, but relatively weak, layers of water-insoluble material which lack sufficient strength to maintain their structural integrity upon dissolution of the primary components of the collector. Interior passage 34 includes a thin protective layer 34a of water-insoluble material so that collected fluid will not prematurely initiate dissolution of the evacuation passage means. A tubular spike 35 projects upwardly and outwardly from the wall on the lower body section 11a and its lumen constitutes an extension of the evacuation passage means 33. As shown most clearly in FIGS. 3 and 5, the spike is provided with a pointed upper end 36 spaced slightly below the stopper 37 of a conventional air-evacuated collection tube 38. The spike may be formed from a rigid plastic or metal and will typically be constructed of a water-insoluble material. Preferably, the spike has a length of approximately 0.5 to 1.5 inches, preferably one inch, so that the tubular spike may be flushed with the device in a common flush toilet without obstructing the water discharge lines.

The collection tube may be of the same type commonly used with double-pointed needles for the collection of blood samples, such as, for example, the collection tubes sold under the "Vacutainer" designation by Becton, Dickinson & Company, Rutherford, N.J. The collection tube 38 is snugly but slidably supported within the support means 32 that extends alongside body 11. Normally, the tube 38 is supported above the tip or spike 35 as shown in FIG. 3. After a midstream sample has been collected within cup 20, the collection tube 38 is urged axially downward in the direction represented by arrow 39 in FIG. 5 to cause the tip 36 of spike 35 to pierce the membrane of stopper 37. Since the tube 38 is supplied in evacuated condition, piercing of the membrane causes liquid to flow from cup 20 into the collection tube (FIG. 5). The stopper 37 is self-sealing, which is well known in the art; hence, upon removal of the collection tube from the collector 10, stopper 37 automatically shields and protects the collection sample from contamination. In this manner, the device automatically extracts the relatively uncontaminated midstream portion, allowing the initial and terminal portions of the stream to pass through the device and into the toilet. Following urination, the collector 10 is simply placed upon a stable support surface, and the patient, nurse or other person urges the air-evacuated collection tube 38 axially downward to cause the collection sample to be transferred from the cup member to the tube. Thereafter, the device may be discarded in the water of a toilet bowl so that the primary layers of the tubular body and the cup member, as well as the support means and the evacuation passage means, dissolve or disperse and the protective inner layers sufficiently disintegrate so that the entire collector, including the short tubular spike, may be safely flushed through the water discharge lines of a waste water treatment system.

It has been noted that the outer surface 20a of the cup member is formed from the water-soluble primary layer but is left exposed to fluid passing through flow passage 14. While it is believed that fluid flowing through the passage only randomly contacts the outer surface for a limited period of time, it may be desirable in some applications to provide means for protecting the outer surface from at least the initial surge of the urine stream. Urine deflection means may therefore be provided around the mouth of the cup member for deflecting urine passing through the passage away from the exposed outer surface of the cup member.

In the construction illustrated in FIGS. 1–5, the urine deflection means may take the form of collar 29 which projects outward from cup member 20 and beyond the cup member's outer surface 20a so that fluid passing through the passage will impinge upon the collar and be directed outward away from the outer surface of the cup member as most clearly illustrated in FIG. 4 by arrow 40. Collar 29 may include a sloped surface 29b which forms the uppermost part of the collar and which extends along an inclined plane away from the cup member for directing fluids flowing through the passage in an outward direction away from the exposed outer surface of the cup member.

The embodiment of FIGS. 6 and 7 is the same as that of FIGS. 1–5 except that deflecting means 50 are provided within the flow passage 14 of the funnel-shaped body 11 for protecting the cover or membrane 26 against tearing that might otherwise result if it were squarely impacted by a forceful initial stream of urine at the beginning of a voiding process. The deflecting means includes a generally horizontal disc-shaped shield 51 located directly above cover 26 and, in particular, above the central upper portion 26a of the dome-shaped cover. It is believed preferable for the shield to have a diameter smaller than that of the cover so that the central upper portion of the cover is protected against frontal impact by the stream but is exposed to less direct or glancing impact by peripheral portions of the same stream so as to commence the process of dissolving the soluble cover. Also, where the shield is substantially smaller in diameter than the cover, urine deflected by the shield may still contact portions of the cover not directly below the shield, as indicated by arrows in FIGS. 6 and 7.

The shield 51 is supported above the cover by an integral support arm 52 connected to a mounting ring or collar 29'. The collar 29' is similar to collar 29 of FIGS. 1–5, serving the functions of holding the cover 26 in place and also, because of its downwardly and outwardly sloping outer surface 29b', providing means for deflecting urine away from the outer surface of cup member 20.

In the embodiment of FIGS. 6 and 7, the disc-shaped shield 51 is imperforate and has a convex upper surface. While convexity is considered desirable, the upper surface may instead be planar or of other contour. The shield may also be perforate as long as it still functions to dissipate the force of the initial stream and prevent tearing or rupturing of the cover 26. Thus, in the embodiment of FIG. 8, the structure is identical to that of FIGS. 6 and 7 except that shield 51' is provided with a multiplicity of small openings 53 which allow liquid to pass through the disc and contact the cover directly beneath it while at the same time preventing the cover from becoming torn by reason of forceful fluid impact.

In each of the embodiments illustrated in FIGS. 6–8, the collector components are illustrated as being flushable as already described in connection with the construction of FIGS. 1–5. Thus, body 11 has a primary outer layer 18 of water-soluble polymeric material and a thin inner protective layer 19 of a water-insoluble material. The same is true of deflecting means 50. Disc 51, arm 52, and collar 29' are all formed primarily of a water-soluble polymer, as previously described, but have their upper surfaces provided with layers 51a, 52a, and 29a', respectively, composed of a protective water-insoluble polymeric material. However, it is to be understood that, if desired, all such components may instead be formed entirely of water-insoluble material (except, of course, for the dome-shaped cover) because effective operation of the deflecting means 50 does not depend on the flushability or non-flushability of the collector.

While in the foregoing I have disclosed embodiments of the invention in considerable detail for purposes of illustration, it will be understood by those skilled in the art that many of these details may be varied without departing from the spirit and scope of the invention.

I claim:

1. A midstream urine collector comprising a funnel-shaped body having a downwardly-tapering wall defining an upper inlet, a lower outlet, and a flow passage therebetween; a cup member having an upwardly-directed mouth and being mounted within said passage below said inlet; said cup member being substantially smaller than said passage to permit the downward flow of urine through said passage past said cup member; a generally dome-shaped cover extending over said cup member formed of a non-contaminating water-soluble polymeric material capable of disintegrating within 2 to 15 seconds upon exposure to a stream of urine; and deflecting means mounted within said body above said cover for shielding at least an upper portion of said cover against direct impingement by a stream of urine discharged into the inlet of said funnel-shaped body.

2. The collector of claim 1 in which said deflecting means comprises a generally horizontal disc-shaped shield.

3. The collector of claim 2 in which said shield has a diameter smaller than that of said dome-shaped cover.

4. The collector of claim 2 in which said shield is generally imperforate.

5. The collector of claim 2 in which said shield has openings therethrough.

6. The collector of claim 2 in which said shield is provided with mounting means connected to said cup member.

7. The collector of claim 6 in which said mounting means comprises a support arm having an upper end joined to said shield and a lower end connected to a mounting collar.

8. The collector of claim 7 in which said mounting collar extends about said cup member.

9. The collector of claim 8 in which said mounting collar has a downwardly and outwardly sloping upper surface for deflecting urine away from said cup member.

10. The collector of claim 1 in which said funnel-shaped body has inner and outer surfaces and is composed of a primary layer of water-soluble material which will dissolve or disperse when disposed in the water of a toilet bowl and a thin protective, but relatively weak, layer of water-insoluble material which lines said inner surface and prevents urine passing through said flow passage from contacting said primary layer; said cup member having an outer surface which is exposed to said flow passage and an inner surface which defines an interior chamber below an upwardly-directed mouth; said cup member being composed a primary layer of water-soluble material which forms the outer surface of the cup member and which will dissolve or disperse when disposed in the water of a toilet bowl and a thin protective, but relatively weak, layer of water-insoluble material which lines said inner surface of said chamber.

11. The collector of claim 10 in which said deflecting means comprises a generally disc-shaped shield supported by a support arm having a lower end connected to a collar extending about said cup member; said shield, arm and collar being primarily formed of water-soluble material having upwardly and outwardly facing surface portions covered by thin layers of water-insoluble material.

* * * * *